(12) United States Patent
Mills et al.

(10) Patent No.: US 11,806,497 B2
(45) Date of Patent: Nov. 7, 2023

(54) ADAPTOR FOR CONNECTING A DRUG DELIVERY DEVICE TO A CONNECTOR

(71) Applicant: Becton Dickinson France, Le Pont de Claix (FR)

(72) Inventors: Freddy Mills, Fontanil Cornillon (FR); Lionel Maritan, Pierre-Chatel (FR); Marc Flippe, Claix (FR)

(73) Assignee: Becton Dickinson France, Le Pont de Claix (FR)

( * ) Notice: Subject to any disclaimer, the term of this patent is extended or adjusted under 35 U.S.C. 154(b) by 420 days.

(21) Appl. No.: 16/497,515

(22) PCT Filed: Mar. 27, 2018

(86) PCT No.: PCT/EP2018/057810
§ 371 (c)(1),
(2) Date: Sep. 25, 2019

(87) PCT Pub. No.: WO2018/178094
PCT Pub. Date: Oct. 4, 2018

(65) Prior Publication Data
US 2020/0114139 A1    Apr. 16, 2020

(30) Foreign Application Priority Data

Mar. 31, 2017 (EP) .................................... 17305388

(51) Int. Cl.
*A61M 39/10* (2006.01)
*A61M 5/14* (2006.01)

(52) U.S. Cl.
CPC ........... *A61M 39/1011* (2013.01); *A61M 5/14* (2013.01); *A61M 2039/1038* (2013.01)

(58) Field of Classification Search
CPC .. A61M 39/1011; A61M 39/10; A61M 39/16; A61M 39/02; A61M 39/00;
(Continued)

(56) References Cited

U.S. PATENT DOCUMENTS 1,933,117 A * 10/1933 Markle .................... F16L 55/10
411/429
3,447,819 A * 6/1969 Borsum .............. F16L 37/0982
277/609

(Continued)

FOREIGN PATENT DOCUMENTS

CN        1272064 A    11/2000
CN      101111282 A     1/2008
(Continued)

*Primary Examiner* — Emily L Schmidt
*Assistant Examiner* — Alexandra Lalonde
(74) *Attorney, Agent, or Firm* — The Webb Law Firm

(57) ABSTRACT

An adaptor includes a tubular body having a proximal region and a distal region, the proximal region configured to engage a distal tip of a drug delivery device and the distal region being configured to be connected to a connector. The distal region has a distal end delimiting a distal opening so as to permit introduction of the connector inside the distal region. The distal end is configured to be clamped to the connector when the connector is introduced inside the tubular body. The distal end includes a deformable element having a free end, which is configured to deform towards the proximal region when the connector is introduced inside the tubular body.

19 Claims, 3 Drawing Sheets

(58) Field of Classification Search
CPC .......... A61M 39/22; A61M 2039/1038; A61M 2039/1033; A61M 2039/261; A61M 2039/267; A61M 2039/268; A61M 2039/1077; A61M 39/0693; A61M 39/1055; A61M 39/12; A61M 2039/1027; A61M 5/14; A61J 1/2048; A61J 1/2096; F16L 37/0987

See application file for complete search history.

(56) References Cited

U.S. PATENT DOCUMENTS

| | | | |
|---|---|---|---|
| 4,084,827 A * | 4/1978 | Wolf | F16L 21/022 |
| | | | 277/625 |
| 4,743,051 A * | 5/1988 | Proni | F16L 37/0987 |
| | | | 285/320 |
| 5,957,898 A | 9/1999 | Jepson et al. | |
| 7,044,441 B2 | 5/2006 | Doyle | |
| 8,888,758 B2 | 11/2014 | Mansour et al. | |
| 9,968,771 B2 | 5/2018 | Wong | |
| 10,933,228 B2 | 3/2021 | Hallynck | |
| 2005/0087715 A1 | 4/2005 | Doyle | |
| 2006/0192164 A1 * | 8/2006 | Korogi | A61B 5/15003 |
| | | | 251/149 |
| 2008/0287920 A1 * | 11/2008 | Fangrow | A61M 39/22 |
| | | | 604/535 |
| 2012/0153613 A1 * | 6/2012 | Kauppi | A61M 39/10 |
| | | | 285/374 |
| 2020/0114139 A1 | 4/2020 | Mills et al. | |

FOREIGN PATENT DOCUMENTS

| | | |
|---|---|---|
| CN | 102131542 A | 7/2011 |
| CN | 209270333 U | 8/2019 |
| EP | 0116986 A1 | 8/1984 |
| EP | 0998325 A2 | 5/2000 |
| JP | S55-158315 U | 11/1980 |
| JP | S59-196718 U | 12/1984 |
| JP | 2005000466 A | 1/2005 |
| JP | 2008522729 A | 7/2008 |
| JP | 2016520388 A | 7/2016 |
| JP | 2016525003 A | 8/2016 |
| WO | 2010028040 A1 | 3/2010 |

* cited by examiner

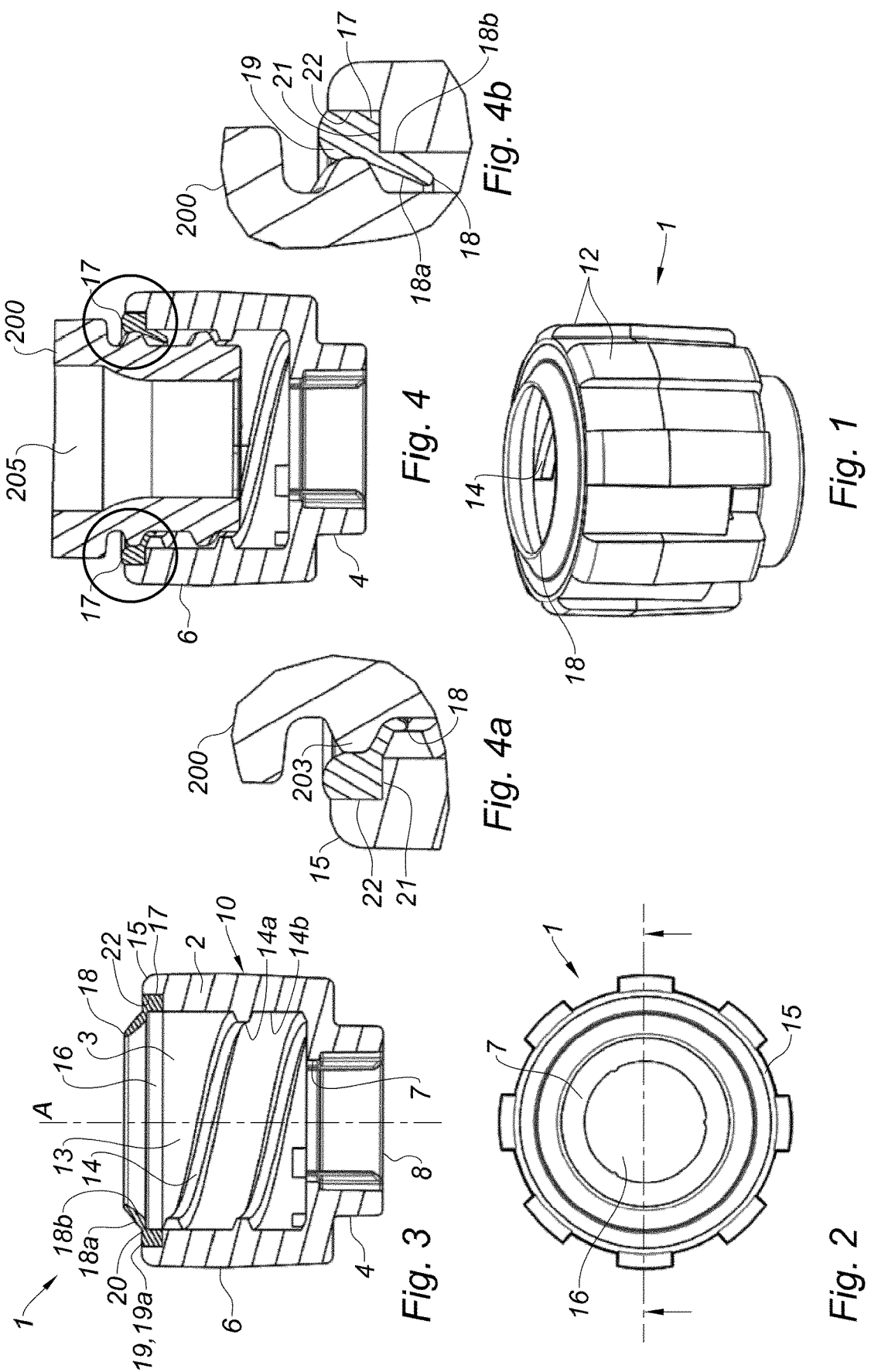

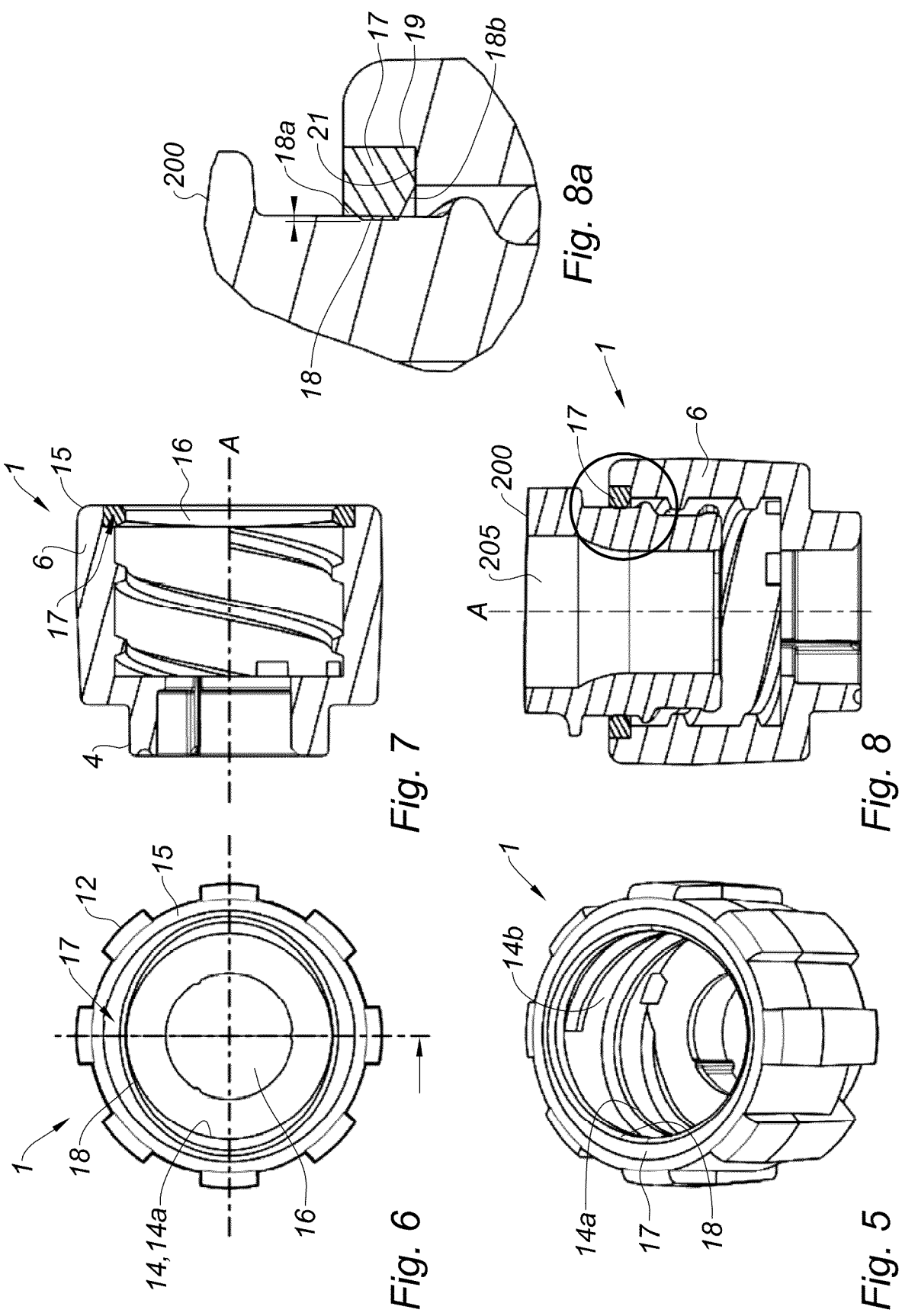

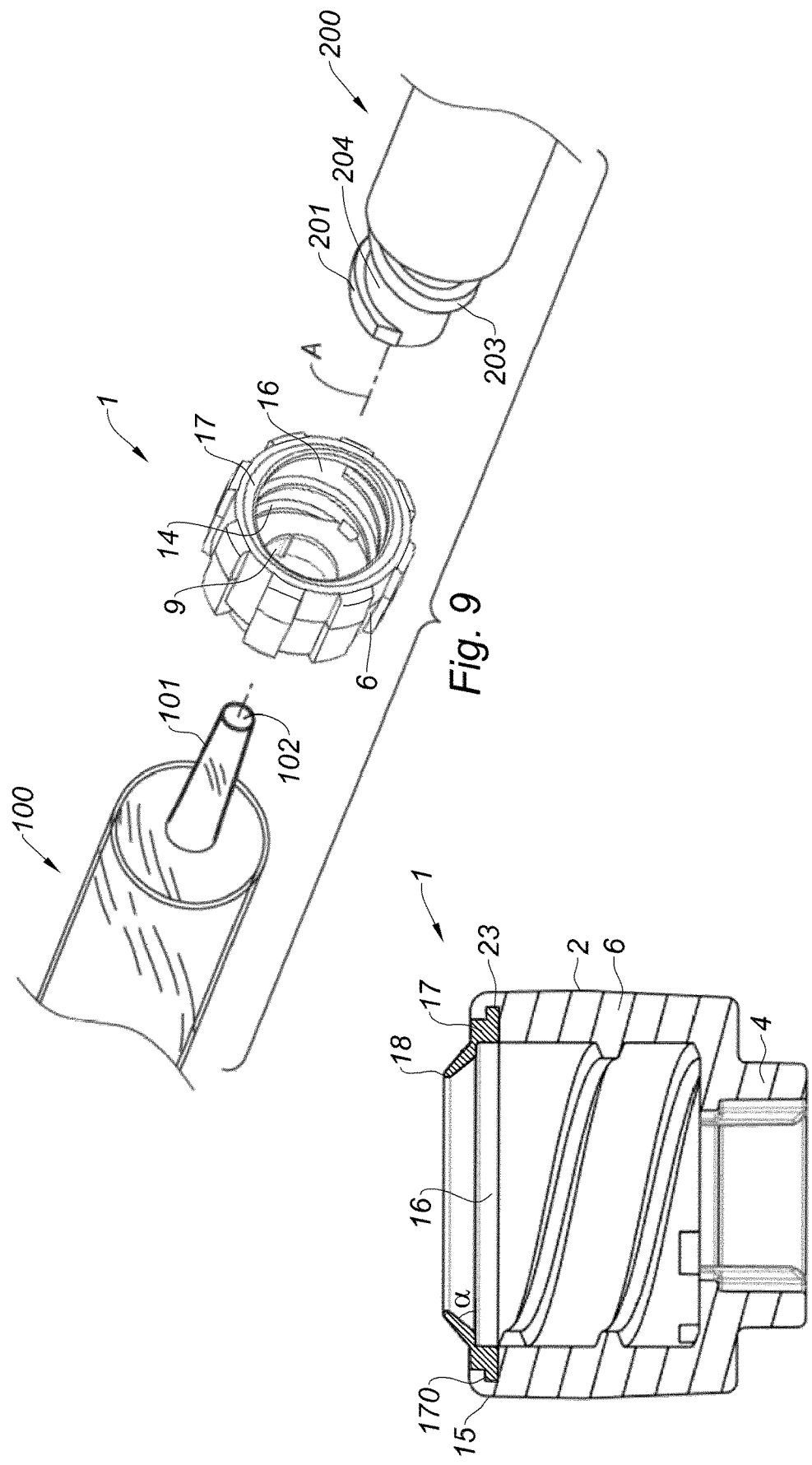

ADAPTOR FOR CONNECTING A DRUG DELIVERY DEVICE TO A CONNECTOR

CROSS-REFERENCE TO RELATED APPLICATIONS

This application is the United States national phase of International Application No. PCT/EP2018/057810 filed Mar. 27, 2018, and claims priority to European Patent Application No. 17305388.5 filed Mar. 31, 2017, the disclosures of which are hereby incorporated by reference in their entirety.

The present invention relates to an improved adaptor, for example a luer lock adaptor, for connecting a drug delivery device to a connector such as a needleless access device. The invention also relates to a drug delivery device provided with such an improved adaptor, to a method for mounting a connector onto said adaptor, and to a method for connecting a drug delivery device to a connector via such an adaptor.

BACKGROUND OF THE INVENTION

Various medical devices are known for transferring and/or storing medical fluids, such as syringes, needle assemblies, perfusion devices, transfusion devices and connectors such as for example IV (Intra Venous), IM (Intra Muscular), subcutaneous connectors or needleless access devices. It is essential for safety reasons that these various medical devices can be assembled together correctly and securely. The use of specific adaptors between the various medical devices allows them to be assembled, ensuring a sealed connection and providing protection against the contamination of the medical liquid products they contain.

A conventional drug delivery device, such as a hypodermic syringe, usually comprises a hollow body forming a container for a medical product. The distal end of the body forming the container usually comprises a longitudinal tip in which an axial passageway is arranged and through which said medical product is expelled from the container into a connector.

In this application, the distal end of a component or of a device is to be understood as meaning the end furthest from the user's hand and the proximal end is to be understood as meaning the end closest to the user's hand. Likewise, in this application, the "distal direction" is to be understood as meaning the direction of injection, with respect to the drug delivery device the adaptor of the invention is intended to be mounted on, and the "proximal direction" is to be understood as meaning the opposite direction to said direction of injection, that is to say the direction towards the user's hand.

In order to transfer the medical product from the drug delivery device to the connector, the connection between the drug delivery device and the connector is usually completed via an adaptor. The adaptor thus allows the transfer of medical product from the drug delivery device to the connector.

Usually, an adaptor intended to be mounted on the distal tip of a drug delivery device comprises a collar fixed to the drug delivery device and surrounding said distal tip, said collar comprising means for connecting the connector to the adaptor, and therefore to the drug delivery device.

A luer lock adaptor is such a collar further provided with a lock or locking means, such as an internal thread capable of cooperating with a corresponding external thread located on the connector, so that the connection between the connector and the drug delivery device via the adaptor is optimized.

The adaptor may be used either with drug delivery devices made of glass or plastic. When drug delivery devices are made of plastic, the collar surrounding the distal tip may be unitarily molded with the drug delivery device. However, drug delivery devices made of glass usually have a separate collar securely mounted to their distal tip.

The adaptor is usually first mounted on the distal tip of the drug delivery device. The connector intended to be connected to the drug delivery device, such as a needle hub for example, may then be screwed into the adaptor in a second step.

However, it may happen that a connector spontaneously unscrews from the adaptor it was previously screwed in, and as a consequence, the connector is accidently disconnected from the drug delivery device. This phenomenon may be increased when the drug delivery device and its distal tip are made of glass, as glass surfaces are naturally easy sliding surfaces. Besides, some connectors are provided with internal safety systems which usually comprise a spring or valve biased piece that needs to be displaced in order to establish the connection with the drug delivery device and further allow access to the drug product. The presence of such springs and/or valves provide the connectors with high counter forces which need to be fought against at the time the connector is connected to the drug delivery device and during the time the connector is connected to the drug delivery device via the adaptor.

Therefore, there is a need for an improved adaptor to ensure a reliable assembly of connector into the adaptor, yet without having to apply too high a torque at the time the needleless access device is screwed into the adaptor. Indeed, increasing the torque for screwing a needleless access device into an adaptor mounted on the distal tip of a drug delivery device increases the risk that the adaptor rotates around the distal tip of the drug delivery device. Such a rotation is not desirable as it weakens the fixation of the adaptor on the distal tip and it does not allow the user to determine whether the needleless access device is correctly screwed into the adaptor or not.

SUMMARY OF THE INVENTION

A first aspect of the invention is an improved adaptor for connecting a drug delivery device to connector which substantially limits the risks of an inadvertent disconnection of the connector.

The adaptor comprises a tubular body, said tubular body having a proximal region and a distal region, the proximal region being provided with engaging means for mounting the adaptor on a distal tip of said drug delivery device and the distal region being provided with a connection element or connecting means for connecting the adaptor to the connector, said distal region having a distal end delimiting a distal opening so as to permit introduction of the connector inside the distal region of the tubular body, wherein the distal end comprises a clamp or clamping means so as to clamp the connector as soon as said connector is introduced inside the tubular body, and wherein the clamp or clamping means comprise at least one deformable element having a free end, said free end being configured to deform towards the proximal region when the connector is introduced inside the tubular body.

Therefore, the adaptor provides a reliable and easy connection.

Indeed, the deformable element facilitates the introduction of the connector inside the adaptor, while exerting both a radial pressure and an axial friction against axial removal of said connector. The unscrewing torque is consequently increased. This substantially reduces a risk of spontaneous disconnection of the connector from the drug delivery device via the adaptor.

Besides, the free end of the deformable element is directed towards the proximal region of the adaptor in an engagement position wherein the connector is inserted inside the distal region of the tubular body. Therefore, the free end acts as a ratchet element preventing removal of the connector. The external thread of the connector indeed bumps into the free end of the deformable element and rubs against this free end in case the connector moves axially in the distal direction. The unscrewing torque is consequently increased.

In embodiments, the connection element or connecting means on the adaptor comprise an internal thread having a crest, and the free end of the at least one deformable element inwardly extends beyond a plane tangential to said crest in a rest position wherein the connector is away from the adaptor, for example, when it is not connected into the adaptor.

This ensures interference between the connector and the connecting means as soon as the connector enters the distal region of the tubular body, so that the connection is therefore more reliable.

In embodiments, the clamp or clamping means is shaped so as to make at least part of the connection element or connecting means visible to the user.

Therefore, the user can easily and quickly engage the connector and the connecting means inside the distal region of the adaptor.

In embodiments, the tubular body comprises an internal wall, and the free end of the at least one deformable element comprises a lower side wall configured to lean against said internal wall when the connector is introduced inside the tubular body.

Such a feature increases the unscrewing torque which needs to be applied so as to disconnect the connector and the adaptor and therefore limits risks of accidental disconnection.

In embodiments, the distal end of the tubular body comprises an axial shoulder, the at least one deformable element abutting on said axial shoulder.

More precisely, the deformable element is secured to said axial shoulder. Having a deformable element which leans against the axial shoulder avoids the deformable element being partly or even entirely pulled off when the connector is inserted inside the adaptor. This results in a more reliable connection.

In embodiments, the distal end of the tubular body comprises an inner radial rim, the at least one deformable element abutting on said inner radial rim.

More precisely, the deformable element is secured to said inner radial rim. As a result, when a connector is inserted into the adaptor, the deformable element is deformed while being retained by the inner radial rim. The inner radial rim exerts a reacting force on the deformable element. This accordingly increases the pressure exerted by the deformable element on the connector so that inadvertent removal of the connector is accordingly prevented.

In embodiments, the distal end of the tubular body comprises a groove, and the at least one deformable element comprises a portion located into said groove.

This portion may be a rib having a shape which is complementary to the shape of the groove. Such a groove better secures the clamping means to the tubular body. This limits the risks of pulling out the clamping means.

In embodiments, the free end of the at least one deformable element distally extends at an angle $\alpha$ to a plane substantially parallel to the distal opening in a rest position wherein the connector is away from the adaptor.

As a result, the pressure exerted by the deformable element on the connector in an engagement position increases, limiting a risk of disconnection of the connector from the adaptor.

The free end of the at least one deformable element may extend outside the tubular body of the adaptor in a rest position wherein the connector is away from the adaptor. When the user wants to connect the connector to the drug delivery device via the adaptor, the connector thus firstly contacts the deformable element. Then, the deformable element consequently begins to bend before the connector engages the connection element or connecting means. As a result, the user can still easily connect the connector to the adaptor.

The free end of the at least one deformable element may fully extend inside the tubular body in an engagement position. Therefore, there is no access to the deformable element when the connector is engaged inside the distal region of the tubular body. This prevents inadvertent damaging impacts on said deformable element.

In embodiments, the free end of the at least one deformable element comprises a rounded or chamfered upper side wall.

Such a feature makes it easy for a user to introduce the connector inside the adaptor, while limiting risks of inadvertent disconnection between the connector and the adaptor. Indeed, the contact area between the connector and the free end of the deformable element is greater in the engaged position, so that the friction forces increase.

In embodiments, the at least one deformable element comprises a base portion, said base portion being secured to the distal end of the tubular body of the adaptor, and a connecting portion, said connecting portion connecting the base portion to the free end, and wherein the connecting portion is substantially thinner than both the base portion and the free end of the at least one deformable element.

Such embodiments have the advantage of facilitating introduction of the connector inside the distal region of the adaptor for the user.

The connecting portion may be connected at an upper part of the base portion. Having a connecting portion extending from a lateral side of an upper part of the base portion improves the radial pressure that the deformable element exerts on the connector and therefore limits risks of an inadvertent disconnection.

In embodiments, the free end of the at least one deformable element has an inwardly decreasing cross section width. In other words, the deformable element becomes slimmer and slimmer towards its free end.

Such embodiments also facilitate insertion of the connector inside the adaptor without compromising reliability of the connection between said connector and adaptor.

In embodiments, the at least deformable element is elastically deformable.

Such a feature allows for reuse of the adaptor without compromising the reliability of the connection.

Another aspect of the invention is a drug delivery device comprising a distal tip, said distal tip defining an axial passageway for the transfer of a product contained in said drug delivery device, wherein the distal tip of the drug delivery device further comprises an adaptor as described herein.

Another aspect of the invention is a method for connecting a connector onto an adaptor as described herein, wherein the method comprises the steps of:

sagging the free end of the at least one deformable element towards the proximal region of the adaptor by slidingly engaging said connector through the distal opening of the adaptor, engaging an external wall of said connector, in particular a connection element or connecting means such as a thread, with the connection element or connecting means of the distal region of the adaptor so as to secure the connector to the adaptor.

The step of sagging the free end by slidingly engaging the connector inside the adaptor is preferably executed before the step of engaging the external wall of the connector with the connecting means of the adaptor.

The external wall of the connector may comprise a protrusion, such as a thread, and the method comprises the step of inserting the connector inside the adaptor at least until the free end is located behind said protrusion, preferably until the proximal end of the connector reaches a point of contact on the distal tip (for example when the internal diameter of the connector leans against the distal tip or frustoconical distal tip). Therefore, the free end acts as a ratchet element so as to limit the risks of accidental disconnection.

According to another aspect of the invention, an adaptor for connecting a drug delivery device to a connector is provided. The adaptor includes: a tubular body having a proximal region and a distal region, wherein the proximal region is configured to engage a distal tip of said drug delivery device and the distal region comprises a connection element for connecting the adaptor to the connector. Said distal region has a distal end delimiting a distal opening which permits introduction of the connector inside the distal region of the tubular body. The distal end comprises at least one clamp configured to clamp the connector as soon as said connector is introduced inside the tubular body. The clamp comprises at least one deformable element having a free end, said free end being configured to deform towards the proximal region when the connector is introduced inside the tubular body.

According to another aspect of the disclosure, a drug delivery device is provided. The drug delivery device includes a distal tip defining an axial passageway for transfer of a product contained in said drug delivery device, wherein the distal tip of the drug delivery device comprises an adaptor for connecting the drug delivery device to a connector. The adapter comprises a tubular body having a proximal region and a distal region, wherein the proximal region is configured to engage the distal tip of said drug delivery device and the distal region comprises a connection element for connecting the adaptor to the connector, said distal region having a distal end delimiting a distal opening which permits introduction of the connector inside the distal region of the tubular body. The distal end comprises at least one clamp configured to clamp the connector as soon as said connector is introduced inside the tubular body. The clamp comprises at least one deformable element having a free end, said free end being configured to deform towards the proximal region when the connector is introduced inside the tubular body.

According to another aspect of the disclosure, a method for connecting a connector onto an adaptor for connecting a drug delivery device to the connector is provided. The method includes providing an adaptor. The adaptor comprises: a tubular body having a proximal region and a distal region, wherein the proximal region is configured to engage a distal tip of said drug delivery device and the distal region comprises a connection element for connecting the adaptor to the connector, said distal region having a distal end delimiting a distal opening which permits introduction of the connector inside the distal region of the tubular body. The distal end comprises at least one clamp configured to clamp the connector as soon as said connector is introduced inside the tubular body. The clamp comprises at least one deformable element having a free end, said free end being configured to deform towards the proximal region when the connector is introduced inside the tubular body. The method further comprises: sagging the free end of the at least one deformable element towards the proximal region of the adaptor by slidingly engaging said connector through the distal opening of the adaptor; and engaging an external wall of said connector with the connection element of the distal region of the adaptor so as to secure the connector to the adaptor.

BRIEF DESCRIPTION OF THE DRAWINGS

The invention and the advantages arising therefrom will clearly emerge from the detailed description that is given below with reference to the appended drawings as follows:

FIG. 1 is a perspective view of an adaptor according to an embodiment of the invention, FIG. 2 is a top view of the adaptor of FIG. 1, FIG. 3 is a cross section view of the adaptor of FIGS. 1 and 2, FIG. 4 is a cross section view of the adaptor of FIGS. 1 and 2 wherein a connector is being inserted into the adaptor, FIGS. 4a and 4b are details of the adaptor of FIG. 4, FIG. 5 is a perspective view of an adaptor according to an embodiment of the invention, FIG. 6 is a top view of the adaptor of FIG. 5, FIG. 7 is a cross section view of the adaptor of FIGS. 5 and 6, FIG. 8 is a cross section view of the adaptor of FIGS. 5 and 6, into which a connector has been represented so as to illustrate an interference portion of the deformable element and the connector, FIG. 8a is a detail of the adaptor of FIG. 8, FIG. 9 is a perspective view of a drug delivery device, an adaptor and a connector according to an embodiment of the invention, FIG. 10 is a cross section view of an adaptor according to an embodiment of the invention.

DETAILED DESCRIPTION OF THE PREFERRED EMBODIMENTS

With reference to FIGS. 1 and 9, is shown an adaptor 1 of the invention, for connecting a drug delivery device 100 to a connector 200.

The adaptor 1 is intended to be mounted on a distal tip 101 of the drug delivery device 100, for example a hypodermic syringe. The distal tip 101 defines an axial passageway 102 for the transfer of a product contained in the drug delivery device 100. The adaptor 1 has a longitudinal axis A aligned on said axial passageway 102.

The distal tip 101 may be made of plastic or glass material. In embodiments, the distal tip 101 is made of glass material. In another embodiment, the distal tip 101, as well as the drug delivery device 100, is made of plastic material selected from crystal clear polymer (CCP), Cyclo Olefin Polymers (COP), Cyclo Olefin Copolymers (COC), acrylonitrile butadiene styrene (ABS), polycarbonate (PC), polystyrene (PS), polypropylene (PP), polyethylene (PE), and their combinations.

The connector 200 intended to be connected onto the drug delivery device 100 thanks to the adaptor 1 of the invention may be any device capable of being connected into the adaptor 1, either for allowing the transfer of a product from the drug delivery device 1 to another medical device, such as a needle hub (Subcutaneous line), a pocket drip, a vial, an IV (Intra Venous) line, an IM (Intra Muscular) line or on the contrary for safely closing the filled drug delivery device 100 before its use and for preventing any contamination, like for example a closure cap in a storage position of the drug delivery device.

In particular, the connector 200 may be a needleless access device, intended to be connected into the adaptor, either for allowing the transfer of a product from the drug delivery device to another medical device, such as a pocket drip, a vial, an IV (Intra Venous) line, an IM (Intra Muscular) line, a SC (SubCutaneous) line, a catheter, or on the contrary for safely closing the filled drug delivery device before its use and for preventing any contamination, like for example a closure cap in the storage position of the drug delivery device.

In the example shown, the connector 200 is intended to be provided with a connection element or connecting means, such as an external thread 201, capable of cooperating with a corresponding connection element or connecting means located on the adaptor 1 as will be explained below. The external thread 201 is provided with a thread crest 203 protruding from an external wall 204. With reference to FIG. 4, the connector 200 delimits an inner passageway 205 in order to permit the transfer of the drug product contained in the drug delivery device 100 to the connector 200 via the adaptor 1. When connected to the connector 200, this passageway 205 is aligned with the longitudinal axis A and aligned with the axial passageway 102 of the distal tip 101 when the adaptor 1 is mounted of the distal tip 101.

As shown for example on FIG. 3, the adaptor 1 comprises a tubular body 2 delimiting a central bore 3 which extends around the longitudinal axis A. The tubular body 2 has a proximal region 4 and a distal region 6. The proximal region 4 of the tubular body 2 is intended to be mounted onto the distal tip 101 of the drug delivery device 100, whereas the distal region 6 of the tubular body 2 is configured to be connected to the connector 200. As shown on FIGS. 3 and 7, the diameter of the central bore 3 inside the proximal region 4 is less than that of the central bore 3 inside the distal region 6.

The proximal region 4 may comprise an inner radial rim 7 delimiting a proximal opening 8 leading to the central bore 3. The inner radial rim 7 may be radially expandable so as to fit with friction on the distal tip 101 of the drug delivery device 100. As shown on FIG. 9, the distal tip 101 may be frusto-conical. The inner radial rim 7 is configured to engage the drug delivery device 100 and/or form engagement means for engaging the adaptor 1 onto the distal tip 101 of the drug delivery device 100. In other embodiments not shown, the inner rim could show alternative designs as long as these designs allow the rim to be friction fitted or stuck onto the distal tip of the drug delivery device.

The tubular body 2 of the adaptor 1 is made of a first material, for example a plastic material, such as a material selected from polycarbonate (PC), polypropylene carbonate (PPC), polysulfone (PSU), and combinations thereof or the like.

As shown on FIGS. 1-2 and 5-6, the tubular body 2 comprises an external wall 10 which may present a plurality of protrusions 12, for example circumferentially distributed protrusions 12, such as substantially axial ribs. These protrusions 12 form a grip or gripping means for potentially improving the grip of the adaptor 1 by a user.

The adaptor 1 is a luer lock adaptor.

The distal region 6 has an internal cylindrical wall 13 which is provided with an internal thread 14. As will appear from the following description, this internal thread 14 forms a connection element or connecting means for connecting the adaptor 1 to the connector 200 at the time of use of the drug delivery device 100.

The internal thread 14 of the adaptor 1 may comprise a proximal part defining a first major diameter, a distal part defining a second major diameter which is strictly less than the first diameter, and a tapered portion linking the proximal part to the distal part, said tapered portion having a major diameter which varies from that of the first diameter to that of the second diameter, as disclosed in the patent WO2015/011151 filed by the applicant.

In an embodiment not shown, the connection element or connecting means of the adaptor can be a groove provided on the inner face of the cylindrical wall, in which a lug of the connector may be clipped.

The distal region 6 of the adaptor 1 has a distal end 15 which delimits a distal opening 16, said distal opening 16 leading to the central bore 3 so as to permit introduction of the connector 200 inside the adaptor 1.

The distal end 15 comprises at least one deformable element 17 which is intended to be deformed so as to radially press the connector 200 as soon as the connector 200 is inserted inside the adaptor 1. The at least one deformable element 17 forms a clamp or clamping means for clamping the connector 200 as soon as the connector 200 enters the adaptor 1.

As shown on FIGS. 1 and 5, the clamp or clamping means may comprise a single deformable element 17. The deformable element 17 may be a deformable annular ring extending from the distal end 15, preferably along a substantially centripetal direction.

In embodiments (not shown), the clamp or clamping means may comprise several deformable elements 17, which may be protrusions extending from the distal end 15 in a substantially centripetal direction. These deformable elements may be circumferentially distributed, preferably at regular intervals. For example, the clamp or clamping means may comprise two diametrically opposite deformable elements 17.

The deformable element 17 is made of a second material different from the first material of a rest of the adaptor 1 and that is less stiff than the first material. As a consequence, the clamp or clamping means does not damage the connector when the connector engages the adaptor, while nevertheless ensuring a secure connection between thereto. The second material may be a plastically deformable material. In embodiments, the second material may be an elastically deformable material, so that the deformable element 17 and the adaptor 1 may be reliably used several times. For example, the deformable element 17 may be made of any material providing it with the desired flexibility, such as acrylonitrile butadiene styrene (ABS), polycarbonate (PC), polyoxymethylene (POM), polystyrene (PS), polybutylene terephthalate (PBT), polypropylene (PP), polyethylene (PE), polyamide (PA), thermoplastic elastomer (TPE), silicones and rubbers and combinations thereof. The deformable element 17 may be a resilient deformable element 17. The deformable element 17 is advantageously overmolded on the adaptor 1.

The deformable element 17 comprises a resilient free end 18, such as a lip, which is configured to deform and to bend substantially towards the proximal region 4 as soon as the connector 200 is introduced inside the tubular body 2 of the adaptor 1, as visible on FIGS. 4, 4a, 4b. In other words, said free end 18 is configured to be oriented towards the proximal region 4 in an engagement position wherein the connector is inserted inside the adaptor 1. It should be noted that FIGS. 8, 8a illustrate a connector virtually superimposed on the adaptor 1 in order to show an interference portion of the deformable element 17. In an engagement position, the deformable element 17 generally sags towards the proximal region 4, the free end 18 tilting towards the proximal region 4.

Having a free end 18 which points towards the proximal region 4 in an engagement position enables said free end 18 to act as a ratchet element leaning against the thread 201, thereby opposing a removal movement of the connector 200 and increasing the unscrewing torque due to friction and/or contact forces.

Having a free end 18 which extends inwards the central bore 3 and the tubular body 2 also protects said free end 18 from outside damaging impacts which could favor an inadvertent disconnection of the connector 200.

As shown on FIGS. 3 and 7, the free end 18 may be configured to extend in a substantially centripetal direction in a rest position wherein the connector 200 is away from the adaptor 1. In other words, the free end 18 points towards the central longitudinal axis A in a rest position. Having a free end 18 which is oriented towards the longitudinal axis A in a rest position ensures that the connector 200 presses against said free end 18 as soon as the connector 200 is moved inwards the adaptor 1, and preferably before the connector 200 engages the thread 14 of the adaptor 1.

In a rest position shown on FIG. 3, the free end 18 may advantageously be oriented at an angle to a plane substantially perpendicular to the longitudinal axis A, so that the free end 18 also slightly extends distally in a rest position. This angle is preferably less than 50°, for example 45°, so as to facilitate insertion of the connector 200 against deformation of the resilient free end 18.

The free end 18 may extend outside the distal region 6 of the tubular body 2 in a rest position. The free end 18 may fully extend inside the distal region 6 of the tubular body 2 in an engagement position, so as to be protected from impacts. In a rest position, the free end 18 may extend at the level of the distal opening 15, as illustrated on FIG. 7, or above the distal opening 15, as illustrated on FIG. 3.

As visible on FIGS. 3 and 7, the internal thread 14 comprises a thread crest 14a and a thread root 14b, respectively defining alternating peaks and valleys on a cross sectional point of view. In a rest position, the free end 18 centripetally extends inside a virtual cylinder defined by the wall tangential to said peaks of the internal thread 14. A diameter defined by the thread crest 14a may thus be less than that defined between two opposite free ends 18 or two free end portions of the deformable element 17.

FIG. 8a shows that the free end 18 of the deformable element 17 defines an interference portion intended to interfere with the connector 200. The diameter between diametrically opposite free ends 18 or free end portions of the deformable element 17 is thereby lower than the diameter of the external cylindrical wall 204 of the connector 100.

In embodiments, the deformable element 17 or its free end 18 is configured to make at least one part of the internal thread 14 visible to the user looking at the distal end 15 of the adaptor 1 in the longitudinal direction, as shown on FIG. 6. Therefore, the user can accurately and quickly engage the connector 200 with the internal thread 14. In other words, the clamp or clamping means delimits a window which extends straight above the internal thread 14. As shown on FIG. 6, the free end 18 of the deformable element 17 may delimit an oval opening. In other embodiments not shown, the clamp or clamping means may alternatively comprise several spaced apart deformable elements 17 which are circumferentially distributed around the distal opening 16.

As illustrated for example on FIG. 3, the deformable element 17 may comprise a base portion 19, which is secured to the distal end 15 of the distal region 6. The deformable element 17 may also comprise a connecting portion 20 which connects the base portion 19 to the free end 18. The connecting portion 20 is therefore positioned between the base portion 19 and the free end 18. The connecting portion 20 is substantially thinner than both the base portion 19 and the free end 18 and thus forms a portion of least width. This favors the deformation of the free end 18 so that the free end 18 is oriented towards the proximal region 4. The connecting portion 20 is advantageously located at an upper part of the base portion 19. For example the connecting portion 20 is adjacent to an upper side wall 19a of the base portion 19.

The free end 18 may have an inwardly decreasing cross section width. For example, the free end may have a triangular, trapezoidal or rounded shape.

The free end 18 may comprise an upper side wall 18a and a lower side wall 18b. As shown on FIG. 4b, the lower side wall 18b is advantageously configured to bear against the internal wall 14b of the distal region 6 of the tubular body 2 in the engaged position, so as to increase the unscrewing torque which needs to be applied in order to unscrew the connector 200 from the adaptor 1. As visible on FIG. 8a, the upper side wall 18a may have a rounded or chamfered shape in order to allow easy deformation of the free end 18.

In embodiments, the distal end 15 comprises a distally oriented shoulder 21. The deformable element 17, in particular the base portion 19, may be secured to this axial shoulder 21 so as to better resist insertion of the connector 200, as can be seen on FIG. 4a, 4b or 8a.

As shown for instance on FIG. 3, the distal end 15 preferably comprises an inner radial rim 22. This inner radial rim 22 may define the distal opening 16. The deformable element 17 is secured to the inner radial rim 22 so as to increase the pressure exerted by the deformable element 17 onto the connector 200. The inner radial rim 22 may be adjacent to the axial shoulder 21, located distally above the axial shoulder 21.

With reference to FIG. 10, the distal end 15 may comprise a circumferential groove 23 extending around the deformable element 17. The deformable element 17, for example its base portion 19, comprises a rib 170 inserted into this groove 23. Such a groove better secures the deformable element 17 to the tubular body so as to avoid risks of pulling out the deformable element 17. The groove may be located inside the axial shoulder 21 or in the inner radial rim 22. The groove may be a retaining groove such as a dovetail groove. As an alternative or complementary embodiment, the deformable element 17 may also be secure to the tubular body 2 of the adaptor 1 for example by chemical bonding.

The shoulder 21, the inner radial rim 22 or the groove 23 form a retainer or retaining means so as to retain the deformable element 17 secured to the distal end 15.

FIGS. 4 and 9 illustrate different steps of a method for mounting the connector 200 on the adaptor 1 as described herein or on the aforesaid drug delivery device 100 including the adaptor 1.

With reference to FIG. 9, the connector 200 is placed in front of the distal opening 16 and moved along the longitudinal axis A towards the distal region 6 of the adaptor 1. The connector 200 then begins to lean against the deformable element 17, more particularly on its free end 18. During insertion of the connector 200 inside the tubular body 2 of the adaptor 1, the free end 18 progressively sags inwards against the tubular body and towards the proximal region 4. The deformable element 17 begins exerting a radial pressure on the external wall 204 of the connector 200, thereby limiting risks of disconnection before the connector 200 engages the thread 14.

The external thread 201 of the connector 200 engages the internal thread 14 of the adaptor 1 after the free end 18 is bent towards the proximal region 4. The connector 200 is screwed into the adaptor 1 so as to secure the connection. By doing so, the free end 18 goes behind the thread 201 and acts as a ratchet element, thereby further limiting risks of disconnection of the connector 200 from the adaptor 1.

The adaptor of the invention allows a reliable connection of a connector onto the distal tip of a drug delivery device. The risks that the connector unscrews spontaneously and accidently from the adaptor of the invention are very limited.

The invention claimed is:

1. An adaptor for connecting a drug delivery device to a connector, the adaptor comprising a tubular body, said tubular body having a proximal region and a distal region comprising an internal thread, the proximal region being configured to engage a distal tip of said drug delivery device and the distal region being configured to be connected to the connector, said distal region having a distal end delimiting a distal opening so as to permit introduction of the connector inside the distal region of the tubular body, wherein the distal end of said distal region is configured to be clamped to the connector when said connector is introduced inside the tubular body, wherein the adaptor further comprises at least one deformable element having a base portion connected to the distal end of said distal region and a free end comprising an upper side wall and a lower side wall extending radially inward from the base portion, wherein, in a rest position in which the connector is away from the adaptor, the free end of the at least one deformable element extends distally from the base portion, such that the upper side wall and the lower side wall of the free end are distally angled at an angle relative to a plane substantially parallel to the distal opening of the tubular body, and wherein said free end is configured to bend towards the proximal region when the connector is introduced inside the tubular body, such that the upper side wall and the lower side wall of the free end are proximally angled at an angle relative to the plane substantially parallel to the distal opening of the tubular body, and such that the free end of the at least one deformable element is configured to sag and rub against the internal thread of the distal region providing a ratchet limiting removal of the connector from the adaptor.

2. The adaptor according to claim 1, wherein the internal thread comprises a crest, and the free end of the at least one deformable element inwardly extends beyond a plane tangential to said crest in the rest position in which the connector is away from the adaptor.

3. The adaptor according to claim 1, wherein at least a portion of the internal thread is configured to be visible to a user when viewing the distal end of said distal region of the tubular body in a longitudinal direction.

4. The adaptor according to claim 1, wherein the tubular body comprises an internal wall, and the lower side wall of the free end of the at least one deformable element is configured to lean against said internal wall when the connector is introduced inside the tubular body.

5. The adaptor according to claim 1, wherein the distal end of said distal region of the tubular body comprises an axial shoulder, and wherein the at least one deformable element abuts on said axial shoulder.

6. The adaptor according to claim 1, wherein the distal end of said distal region of the tubular body comprises an inner radial rim, and wherein the at least one deformable element abuts on said inner radial rim.

7. The adaptor according to claim 1, wherein the distal end of said distal region of the tubular body comprises a groove, and the base portion of the at least one deformable element is located into said groove.

8. The adaptor according to claim 1, wherein said base portion of the at least one deformable element is secured to the distal end of said distal region of the tubular body of the adaptor, the at least one deformable element further comprising a connecting portion, said connecting portion connecting the base portion to the free end, and wherein the connecting portion is substantially thinner than both the base portion and the free end of the at least one deformable element.

9. The adaptor according to claim 1, wherein the free end of the at least one deformable element has an inwardly decreasing cross sectional width.

10. The adaptor according to claim 1, wherein the at least one deformable element is elastically deformable.

11. The adaptor according to claim 1, wherein the at least one deformable element is configured to exert inwardly directed radial pressure against the connector when the connector is introduced inside the tubular body of the adaptor.

12. The adaptor according to claim 11, wherein the inwardly directed radial pressure against the connector increases an unscrewing torque required for disconnection of the connector from the adaptor.

13. The adaptor according to claim 1, wherein, in the rest position, at least a portion of the upper side wall and at least a portion of the lower side wall of the free end are distal to the distal opening of the tubular body.

14. The adaptor according to claim 1, wherein said free end is configured to bend when the connector is introduced inside the tubular body, such that at least a portion of the upper side wall and at least a portion of the lower side wall of the free end move from the rest position through the distal opening of the tubular body to an engagement position in the distal region of the adaptor.

15. The adaptor according to claim 1, wherein, in the rest position, the upper side wall and the lower side wall of the free end are distally angled by less than 50 degrees relative to the plane substantially parallel to the distal opening of the tubular body.

16. A drug delivery device comprising a distal tip, said distal tip defining an axial passageway for the transfer of a product contained in said drug delivery device, wherein the distal tip of the drug delivery device further comprises the adaptor according to claim 1.

17. A method for connecting a connector onto the adaptor according to claim 1, wherein the method comprises the steps of:
   sagging the free end of the at least one deformable element towards the proximal region of the adaptor by slidingly engaging said connector through the distal opening of the adaptor, and
   connecting an external wall of said connector with the distal region of the adaptor to secure the connector to the adaptor.

18. The method according to claim 17, wherein the connector comprises the external wall comprising an external thread that engages the free end of the at least one deformable element, and wherein the internal thread on the distal region of the adaptor engages the external thread to secure the connector to the adaptor.

19. The method according to claim 18, wherein connecting the external wall of said connector with the distal region of the adaptor comprises rotating the connector relative to the adaptor causing the external thread of the connector to engage the internal thread of the distal region of the adaptor and to rub against the free end of the at least one deformable element providing the ratchet that limits removal of the connector from the adaptor.

* * * * *